United States Patent [19]

Irikura et al.

[11] Patent Number: 4,649,198

[45] Date of Patent: Mar. 10, 1987

[54] IMIDAZO(1,5-A)PYRIMIDINE DERIVATIVES AND THEIR USE AS ANTIMYCOTIC AGENTS

[75] Inventors: Tsutomu Irikura, Tokyo; Seigo Suzue, Kuki; Hiroaki Uchida, Tokyo; Hirotaka Shinoda, Kawaguchi; Satoshi Murayama; Susumu Kinoshita, both of Tochigi, all of Japan

[73] Assignee: Kyorin Pharmaceutical Co., Ltd., Tokyo, Japan

[21] Appl. No.: 629,385

[22] Filed: Jul. 10, 1984

[30] Foreign Application Priority Data

Jul. 12, 1983 [JP] Japan ............................. 58-126697

[51] Int. Cl.$^4$ ................ C07D 487/04; A61K 31/505
[52] U.S. Cl. .................................... 544/281; 544/117
[58] Field of Search ...................... 544/281; 424/251

[56] References Cited

U.S. PATENT DOCUMENTS

| | | | |
|---|---|---|---|
| 3,923,808 | 12/1975 | Van Gelder et al. | 544/281 |
| 4,178,449 | 12/1979 | Dusza et al. | 544/281 |
| 4,236,005 | 11/1980 | Dusza et al. | 544/281 |
| 4,408,047 | 10/1983 | Baldwin et al. | 544/281 |

OTHER PUBLICATIONS

Guerret, P. et al., Chemical Abstract 77:125679z (1972).

Primary Examiner—George F. Lesmes
Assistant Examiner—S. A. Gibson
Attorney, Agent, or Firm—Armstrong, Nikaido, Marmelstein & Kubovcik

[57] ABSTRACT

Imidazo [1,5-a] pyrimidine derivatives of the formula (I) exhibit antifungal properties:

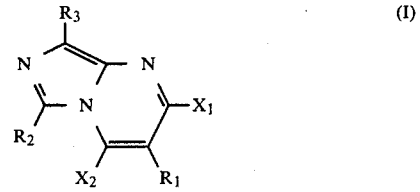

(I)

wherein $X_1$ and $X_2$ are selected from the group consisting of a hydrogen atom, a halogen atom, a hydroxy group, an amino or substituted amino group, an alkoxy group, an alkylthio group, an alkylsulfinyl group and an alkylsulfonyl group; $R_1$, $R_2$ and $R_3$ are selected from the group consisting of a hydrogen atom, an alkyl group, an alkenyl group, an alkynyl group, an aryl group and an aralkyl group.

Compound (I) are prepared by reacting the corresponding α-acylamino-alkylpyrimidines with condensing agents to form chlorine-substituted imidazo [1,5-a] pyrimidines, then replacing one or both chlorine atoms in the pyrimidine ring with other substituents, if necessary.

1 Claim, No Drawings

IMIDAZO(1,5-A)PYRIMIDINE DERIVATIVES AND THEIR USE AS ANTIMYCOTIC AGENTS

This invention relates to novel imidazo[1,5-a]pyrimidine derivatives and process for their preparation. Moreover, it relates to novel imidazo[1,5-a]pyrimidine derivatives and salts thereof having antifungal activities, and process for their preparation.

DETAILED DESCRIPTION OF THE INVENTION

This invention relates to a new class of compound of imidazo[1,5-a]pyrimidine series. It relates also to the synthesis of such substance. It is concerned further with salts of these compounds such as hydrochloride, sulfate, acetate, tartarate and methanesulfonate.

These new compounds of the invention have the general formula (I),

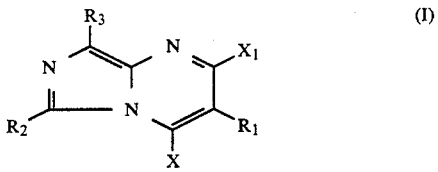

wherein $X_1$ and $X_2$ are selected from the group consisting of a hydrogen atom, a halogen atom, a hydroxy group, an amino or substituted amino group, an alkoxy group, an alkylthio group, an alkylsulfinyl group and an alkylsulfonyl group; $R_1$, $R_2$ and $R_3$ are selected from the group consisting of a hydrogen atom, an alkyl group, an alkenyl group, an alkynyl group, an aryl group and an aralkyl group. The term "alkyl group" in the content of this invention includes continuous or branched chain alkyl group and cyclic alkyl group.

It has been found that these compounds possess valuable pharmacological properties. For instance they produce antifungal effects and may be used for therapeutic properties.

Recently, fungal diseases are on the increase internationally because of frequent use of a broad spectrum of antibiotics, steriod hormones and immunosuppressive agent et cetera. However, useful antifungal agents in the therapy of fungal diseases are limited. At present, the, drugs for fungal diseases are polyenmarcrolide and imidazole derivatives. It has been expected that more useful antifungal agents can be developed for treatment of fungal disease. Therefore, we have studied earnestly to develop compound having more useful activity, especially great potent antifungal activity. As a result of our study, we have found that novel imidazo[1,5-a]pyrimidine derivatives having different structure have high potency against many different organisms as compared with known antifungal agents. The compounds of the present invention and its salts are new compounds which have been not described in any references. The present compounds may be used not only as a medicine for humans, but also drug for animals, including fish and shells, and antiseptic for food in the various forms.

As suitable salts of the compounds represented by the formula (I), are salts derived from inorganic acid, such as, for example, hydrochloric acid, sulfuric acid, or salts derived from organic acid, such as, for example, acetic acid, tartaric acid, methanesulfonic acid, or the like.

These new compounds can be prepared by the method mentioned below.

The α-acylaminoalkylpyrimidine compounds represented by the formula (II) were converted to the imidazo[1,5-a]pyrimidine compounds having the formula (III) by condensing agents such as phosphoryl chloride and thionyl chloride.

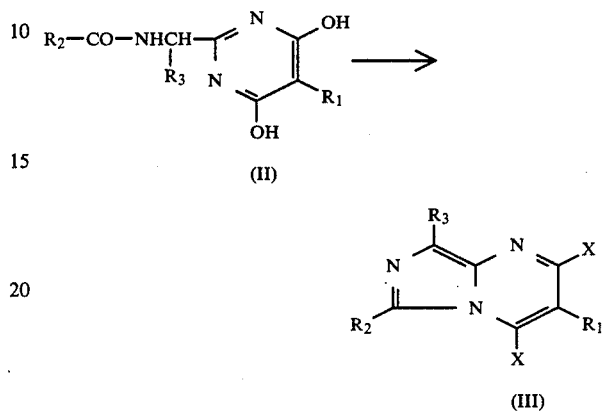

wherein $R_1$, $R_2$ and $R_3$ have the previously defined meanings, X is a halogen atom.

And if necessary, X in the formula (III) can be converted to other substituents. That is, one or two of X can be reduced to hydrogen atom(s), also can be converted to hydroxy group(s), amino or substituted amino group(s), alkoxy group(s) and alkylthio group(s) by the reaction with alkali, ammonia, amines, alcohols and alkylthiolates. Alkylthio group further can be oxidized to alkylsulfinyl or alkylsulfonyl group.

α-Acylaminoalkylpyrimidine compounds having the formula (II), the starting materials in the reaction discussed above, are also novel compounds and can be prepared by two methods. One method of preparation of these compounds involves (a) conversion of the substituted or non-substituted α-aminoacetonitriles to the N-acyl derivatives of aminoacetonitrile using various acid chloride, (b) treatment of the N-acyl derivatives with hydrogen chloride in ethanol followed by treatment with ammonia in ethanol to give the amidine derivatives and (c) reaction of the latter compounds with substituted or non-substituted diethyl malonate to give the desired compound (II). These reactions are summarized in the following scheme.

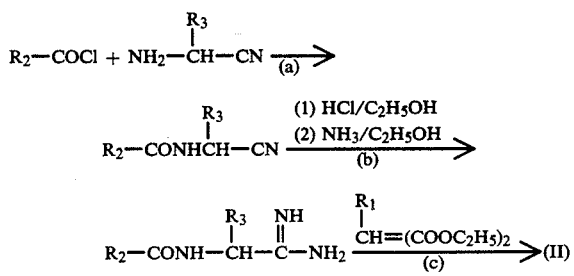

wherein $R_1$, $R_2$ and $R_3$ are as above.

An alternative method for preparing these compounds involves (d) the reaction of α-substituted or non-substituted glycine ethyl ester hydrochlorides with various acid chlorides to give N-acyl derivatives of glycine ethyl ester and (e) treatment of these N-acyl derivatives with substituted or non-substituted malonamide to give the desired compounds (II). These reactions are summarized in the following scheme.

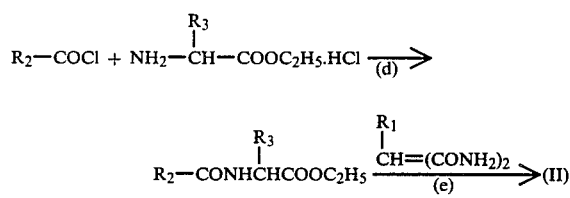

wherein $R_1$, $R_2$ and $R_3$ are as above.

Preparation of intermediate compounds:

EXAMPLE A

Preparation of 2-(3,4-dichlorobenzoylaminomethyl)-4,6-dihydroxypyrimidine (i) The stirred solution of aminoacetonitrile sulfate (42 g) in water (180 ml) is cooled in an ice bath and the solution of sodium carbonate (51 g) in water (250 ml) is added in portions. Then, 3,4-dichlorobenzoylchloride (63 g) is added and the mixture is stirred vigorously for 5 hours at room temperature. Filtration followed by recrystallization from ethanol give acyl derivative (53.9 g).

(ii) Part (i) (53.9 g) is added to the solution of hydrogen chloride gas (68.6 g) in ethanol (500 ml) the mixture is stirred vigorously in an ice bath for 17 hours. Ethanol is evaporated, the residue is poured into ice-water, neutralized by sodium bicarbonate solution, and extracted with chloroform. The chloroform layer is washed with water, dried over sodium sulfate and evaporated to give yellow crystals (50 g).

(iii) Part (ii) (50 g) is added to the ice cooled solution of ammonia gas (247 g) in ethanol (300 ml) and the mixture is stirred for 14 hours. The precipitated crystals are filtered to give amidine derivatives (38.5 g).

(iv) Part (iii) is added to the solution of sodium (5.6 g) in ethanol (250 ml) then diethyl malonate (13 g) is added and the mixture is stirred for 8 hours at 60° C. Ethanol is evaporated, the residue is dissolved in water and washed with ether. The water layer is neutralized with acetic acid. The precipitate is filtered, washed with water and recrystallized from dimethylformamide to give 2-(3,4-dichlorobenzoylaminomethyl)-4,6-dihydroxypyrimidine (11.4 g) as colorless crystal. m.p. 268°–270° C. (dec.)

|  | C | H | N |
|---|---|---|---|
| Anal. (%) Calcd. for $C_{12}H_9N_3O_3Cl_2$: | 45.88 | 2.89 | 13.38 |
| Found: | 45.97 | 2.76 | 13.44 |

Other compounds prepared by the method of this example are as follows.

$$R_2-CO-NHCH\underset{R_3}{\overset{}{-}}\underset{\underset{OH}{\overset{N}{\|}}}{\overset{N}{\diagup}}\overset{OH}{\underset{R_1}{\diagdown}}$$

| $R_1$ | $R_2$ | $R_3$ | m.p. (°C.) |
|---|---|---|---|
| H | phenyl | H | 280–285 (dec.) |
| H | 4-CH₃-phenyl | H | >300 |
| H | 4-Br-phenyl | H | >300 |
| H | 4-CH₃O-phenyl | H | 288–293 (dec.) |
| H | 4-I-phenyl | H | >300 |
| H | 2,3-dichlorophenyl | H | 263–269 (dec.) |
| H | 4-F-phenyl | H | — |
| H | 4-(CH₃)₃C-phenyl | H | — |
| H | 3,4-dichlorophenyl | H | — |

EXAMPLE B

Preparation of 2-(4-chlorobenzylcarbonylaminomethyl)-4,6-dihydroxypyrimidine (i) The mixture of the solution of glycine ethyl ester hydrochloride (38.1 g) and potassium carbonate (150 g) in water (700 ml), benzene (600 ml) and ether (450 ml) is stirred vigorously at room temperature. The solution of 4-chlorophenylacetylchloride (61.5 g) in benzene (100 ml) is added dropwise to above mixture during 30 minutes and stirred for 3 hours. The organic layer is dried over sodium sulfate, evaporated to 200 ml and cooled. The precipitate is filtered to give acyl derivative of glycine ethyl ester (44.1 g) as colorless crystals.

(ii) Malonamide (9.5 g) is added to the solution of sodium (4.04 g) in ethanol (400 ml) and stirred at 50° C. for 1 hour.

Part (i) is added to the mixture and refluxed for 6 hours. Ethanol is evaporated, the residue is dissolved in water and neutalized with acetic acid. The precipitate is filtered, washed with water and recrystallized from dimethylformamide to give 2-(4-chlorobenzylcarbonylaminomethyl)-4,6-dihydroxypyrimidine (9 g) as colorless crystals.

m.p. 280°–283° C. (dec.)

|  | C | H | N |
|---|---|---|---|
| Anal. (%) Calcd. for $C_{13}H_{12}N_3O_3Cl$: | 53.16 | 4.12 | 14.31 |
| Found: | 53.11 | 4.07 | 14.51 |

Additional compounds prepared by the method of this example are as follows.

| $R_1$ | $R_2$ | $R_3$ | m.p. (°C.) |
|---|---|---|---|
| H |  (2,4-dichlorobenzyl) | H | 235–240 (dec.) |
| H |  (2,6-dichlorobenzyl) | H | 284–287 (dec.) |
| H |  (cyclohexyl) | H | 260–265 (dec.) |
| H |  (cyclohexylmethyl) | H | 290–300 (dec.) |
| H | Cl—⌬—CH₂CH₂— | H | 263–265 (dec.) |
| H |  (benzyl) | H | 255–260 (dec.) |
| H | ⌬—CH=CH— | H | 279–283 (dec.) |
| H | ⌬—CH₂CH₂— | H | 245–250 (dec.) |
| H | $H_5C_2OOC$—⌬— | H | 258–264 (dec.) |
| H | 1-adamantyl | H | 195–202 (dec.) |
| H | ⌬—CH(CH₃)— | H | 253–259 (dec.) |
| H | 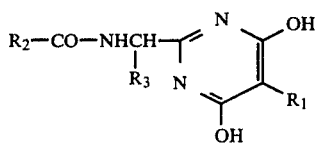 (3-trifluoromethylphenyl) | H | — |
| H | ⌬— | ⌬— (phenyl) | oil |
| H | Br—⌬—CH₂— | H | 265–270 (dec.) |

EXPERIMENT 1

The antifungal activity of the compound of the present invention was assayed by the standard agar dilution streak method against fungi. The results were shown in Table 1. M.I.C. studies with representative members of the compound of this invention have demonstrated extremely favorable antimycotic activity, so that these compounds will be very useful as therapeutic agents, drugs for animals, fishes and shells, and an antiseptic for food.

TABLE 1

Antifungal Activity

| Organismus | Minimum Inhibitory Concentration (μg/ml) | | | | | | | | |
|---|---|---|---|---|---|---|---|---|---|
|  | Ex. 1 | Ex. 5 | Ex. 7 | Ex. 9 | Ex. 16 | Ex. 18 | Ex. 23 | Ex. 20 | Ex. 21 |
| *Candida albicans* 3147 | 6.25 | 1.56 | 1.56 | 1.56 | 1.56 | 3.13 | 1.56 | 0.78 | 1.56 |
| *Candida albicans* IFO-1388 | 1.56 | 1.56 | 1.56 | 0.78 | 1.56 | 0.78 | 0.20 | 0.78 | 3.13 |
| *Candida albicans* IFO-1594 | 3.13 | 3.13 | 1.56 | 3.13 | 1.56 | 3.13 | 0.39 | 0.78 | 6.25 |
| *Candida albicans* MTU-12124 | 3.13 | 3.13 | 1.56 | 1.56 | 6.25 | 3.13 | 6.25 | 0.78 | 1.56 |
| *Candida albicans* KYF-602 | 6.25 | 6.25 | 3.13 | 6.25 | 3.13 | 12.5 | 3.13 | >6.25 | >6.25 |
| *Candida stellatidea* IFO-1398 | 0.20 | 0.20 | 0.39 | 0.78 | 0.78 | 3.13 | 3.13 | 0.20 | 1.56 |
| *Microsporum canis* 20010 | 0.78 | 0.78 | 0.39 | 1.56 | 0.39 | 1.56 | 1.56 | 0.78 |  |
| *Aspergillus fumigatus* MTU-06002 | 6.25 | 6.25 | >100 | 12.5 | 3.13 | 25 | 50 | >6.25 |  |
| *Trichophyton mentagrophytes* MTU-19003 | 1.56 | 1.56 | 0.78 | 1.56 | 1.56 | 1.56 | 3.13 | 1.56 |  |
| *Trichophyton mentagrophytes* MTU-19005 | 0.78 | 0.78 | 0139 | 0.78 | 0.20 | 1.56 | 1.56 | 0.78 |  |

The following examples are further illustrative of this invention.

Preparation of compounds of this invention.

EXAMPLE 1

Preparation of 2,4-dichloro-6-(4-chlorophenyl)imidazo[1.5-a]pyrimidine 2-(4-Chlorobenzoylaminomethyl)-4,6-dihydroxypyrimidine (1 g) is added to phosphoryl chloride (10 ml) and refluxed for 3 hours. Excess phosphoryl chloride is evaporated in vacuo, the residue is neutralized with sodium bicarbonate aqueous solution and extracted with chloroform. The chloroform layer is washed with water, dried over sodium sulfate and evaporated to give a yellowish-brown residue. Purification by alumina column-chromatography (eluted with benzene) followed by recrystallization from ethanol give 2,4-dichloro-6-(4-chlorophenyl)imidazo[1,5-a]pyrimidine (0,.34 g) as yellow prisms.
m.p. 203°–205° C.

|  | C | H | N |
|---|---|---|---|
| Anal. (%) Calcd. for $C_{12}H_6N_3Cl_3$: | 48.28 | 2.03 | 14.07 |
| Found: | 48.30 | 1.85 | 14.05 |

Other compounds prepared by the method of example 1 are as follows.

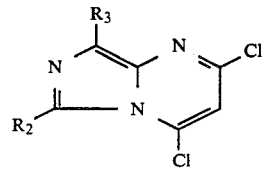

| Ex. No. | R$_2$ | R$_3$ | m.p. (°C.) | Molecular Formula | Anal. (%); Calcd. (Found) C | H | N |
|---|---|---|---|---|---|---|---|
| 2 | phenyl | H | 174–175 | $C_{12}H_7N_3Cl_2$ | 54.57(54.54) | 2.67(2.44) | 15.91(15.98) |
| 3 | 4-CH$_3$-phenyl | H | 163–164 | $C_{13}H_9N_3Cl_2$ | 56.14(56.16) | 3.26(3.08) | 15.11(15.06) |
| 4 | 4-(CH$_3$)$_2$C-phenyl | H | 124–125 | $C_{16}H_{15}N_3Cl_2$ | 60.01(60.18) | 4.72(4.58) | 13.12(13.03) |
| 5 | 4-Br-phenyl | H | 202–203 | $C_{12}H_6N_3BrCl_2$ | 42.02(42.03) | 1.76(1.56) | 12.25(12.27) |
| 6 | 4-F-phenyl | H | 189–190 | $C_{12}H_6N_3Cl_2F$ | 51.09(51.10) | 2.14(1.97) | 14.90(14.87) |
| 7 | 3,4-diCl-phenyl | H | 188–189 | $C_{12}H_5N_3Cl_4$ | 43.28(43.39) | 1.51(1.33) | 12.62(12.72) |
| 8 | 3,5-diCl-phenyl | H | 214–215 | $C_{12}H_5N_3Cl_4$ | 43.28(43.44) | 1.51(1.37) | 12.62(12.62) |
| 9 | 2,3-diCl-phenyl | H | 155–156 | $C_{12}H_5N_3Cl_4$ | 43.28(43.53) | 1.51(1.48) | 12.62(12.52) |

-continued
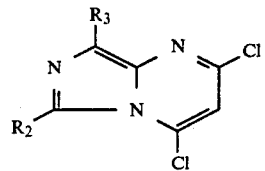
| Ex. No. | R₂ | R₃ | m.p. (°C.) | Molecular Formula | Anal. (%); Calcd. (Found) C | H | N |
|---|---|---|---|---|---|---|---|
| 10 | CH₃O—⟨phenyl⟩— | H | 150–151 | $C_{13}H_9N_3OCl_2$ | 53.08(52.83) | 3.08(3.01) | 14.29(14.23) |
| 11 | CF₃—⟨phenyl⟩— | H | 144–145 | $C_{13}H_6N_3Cl_2F_3$ | 47.02(46.92) | 1.82(1.61) | 12.65(12.68) |
| 12 | H₅C₂OOC—⟨phenyl⟩— | H | 145–146 | $C_{15}H_{11}Cl_2N_3O_2$ | 53.59(53.21) | 3.30(3.18) | 12.50(12.61) |
| 13 | ⟨phenyl⟩—CH₂— | H | 139–140 | $C_{13}H_9N_3Cl_2$ | 56.14(56.08) | 3.26(3.03) | 15.11(15.08) |
| 14 | ⟨phenyl⟩— | ⟨phenyl⟩— | 190–191 | $C_{18}H_{11}N_3Cl_2$ | 63.55(63.47) | 3.26(3.00) | 12.35(12.38) |
| 15 | ⟨phenyl⟩—CH=CH— | H | 215–216 | $C_{14}H_9N_3Cl_2$ | 57.95(58.06) | 3.13(2.92) | 14.48(14.44) |
| 16 | Cl—⟨phenyl⟩—CH₂— | H | 170–171 | $C_{13}H_8N_3Cl_3$ | 49.95(49.85) | 2.58(2.40) | 13.44(13.52) |
| 17 | Cl,Cl—⟨phenyl⟩—CH₂— | H | 163–164 | $C_{13}H_7N_3Cl_4$ | 44.99(45.11) | 2.03(1.92) | 12.01(12.23) |
| 18 | ⟨phenyl⟩—CH(CH₃)— | H | 100–101 | $C_{14}H_{11}N_3Cl_2$ | 57.55(57.51) | 3.79(3.61) | 14.38(14.48) |
| 19 | ⟨phenyl⟩—CH₂CH₂— | H | 155–156 | $C_{14}H_{11}N_3Cl_2$ | 57.55(57.40) | 3.79(3.57) | 14.38(14.45) |
| 20 | Cl,Cl—⟨phenyl⟩—CH₂— | H | 158–159 | $C_{13}H_7N_3Cl_4$ | 44.99(45.07) | 2.03(1.85) | 12.01(12.12) |

-continued

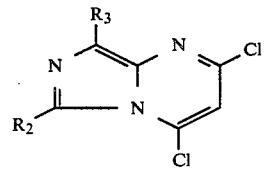

| Ex. No. | R₂ | R₃ | m.p. (°C.) | Molecular Formula | Anal. (%); Calcd. (Found) C | H | N |
|---|---|---|---|---|---|---|---|
| 21 | I-C₆H₄- | H | 197–199 | $C_{12}H_6N_3Cl_2I$ | 36.96(37.07) | 1.55(1.47) | 10.77(10.78) |
| 22 | Cl-C₆H₄-CH₂CH₂- | H | 191–192 | $C_{14}H_{10}N_3Cl_3$ | 51.48(51.44) | 3.09(2.91) | 12.87(12.84) |
| 23 | cyclohexyl- | H | 171–172 | $C_{12}H_{13}N_3Cl_2$ | 53.35(53.45) | 4.85(4.79) | 15.55(15.65) |
| 24 | cyclohexyl-CH₂- | H | 132–133 | $C_{13}H_{15}N_3Cl_2$ | 54.94(54.91) | 5.32(5.22) | 14.79(14.92) |
| 25 | adamantyl- | H | 213–214 | $C_{16}H_{17}N_3Cl_2$ | 59.64(59.65) | 5.32(5.32) | 13.04(13.03) |
| 26 | Br-C₆H₄-CH₂- | H | 152–153 | $C_{13}H_8N_3BrCl_2$ | 43.73(43.44) | 2.26(2.14) | 11.77(11.66) |

The following compounds are synthesized from the product of example 2.

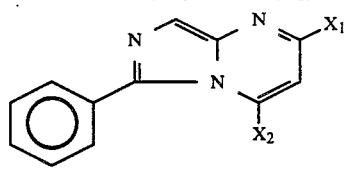

| Ex. No. | X₁ | X₂ | m.p. (°C.) | Molecular Formula | Analysis; Calcd. (Found) C | H | N |
|---|---|---|---|---|---|---|---|
| 27 | —OCH₃ | —OCH₃ | 187–188(dec.) | $C_{14}H_{13}N_3O_2$ | 65.87(65.69) | 5.13(5.02) | 16.46(16.29) |
| 28 | H | H | 124–125 | $C_{12}H_9N_3$ | 73.87(73.97) | 4.65(4.51) | 21.53(21.34) |
| 29 | —SCH₃ | —SCH₃ | 181–183 | $C_{14}H_{13}N_3S_2$ | 58.51(58.70) | 4.56(4.47) | 14.62(14.64) |
| 30 | —NHCH₂-C₆H₅ | Cl | 224–225 | $C_{19}H_{15}N_4Cl$ | 68.16(68.12) | 4.52(4.36) | 16.73(16.62) |
| 31 | morpholino | Cl | 227–229(dec.) | $C_{16}H_{15}N_4OCl$ | 61.05(61.20) | 4.80(4.77) | 17.80(17.81) |

-continued

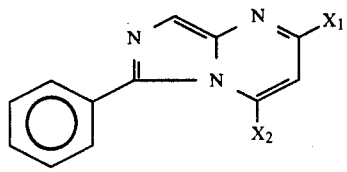

| Ex. No. | X₁ | X₂ | m.p. (°C.) | Molecular Formula | Analysis; Calcd. (Found) | | |
|---|---|---|---|---|---|---|---|
| | | | | | C | H | N |
| 32 | Cl | 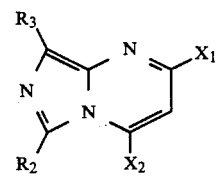 | 234–236 | $C_{16}H_{15}N_4OCl$ | 61.05(61.12) | 4.80(4.68) | 17.80(17.78) |

EXAMPLE 27

The product of example 2 (0.88 g) is added to the solution of sodium (0.3 g) in methanol (30 ml) and refluxed for 3 hours. After evaporation of methanol the residue is washed with water and filtered. Recrystallization from ethanol gives the desired product (0.6 g).

EXAMPLE 28

The product of example 2 (1 g), concentrated ammonia water (2 ml) and 10% palladium carbon (0.2 g) are added to ethanol (50 ml). The mixture is hydrogenated in an autoclave (20 atm at room temperature) for 6 hours. The catalyst is removed by filtration and the filtrate is evaporated in vacuo. Water is added to the residue and extracted with chloroform. The chloroform layer is washed with water, dried over sodium sulfate and evaporated to give yellowish-brown crystal. Purification by alumina column-chromatography (eluted with benzene) followed by recrystallization from benzene-n-hexane gives the desired product (0.2 g).

EXAMPLE 29

The product of example 2 (0.2 g) is dissolved in methanol (20 ml) and methyl mercaptan sodium salt (15% in water) (1.5 g) is added to this. After stirring at room temperature for 30 minutes, the solution is refluxed for 30 minutes. Water is added and an extraction is conducted with chloroform. The chloroform layer is washed with water and dried over sodium sulfate to give yellow crystals.

Purification by alumina column-chromatography (eluted with benzene) followed by recrystallization from ethanol gives the desired product (0.11 g).

EXAMPLE 30

The product of example 2 (0.53 g) and benzylamine (0.43 g) are added to ethanol (20 ml) and refluxed for 8 hours. Water is added and an extraction is conducted with chloroform. The chloroform layer is washed with water, dried over sodium sulfate and evaporated to give the residue. Recrystallization from ethanol gives desired product (0.5 g).

EXAMPLE 31 AND 32

The product of example 2 (0.53 g) and morpholine (0.35 g) are added to ethanol (30 ml) and the mixture is refluxed for 12 hours. Water is added and an extraction is conducted with chloroform. The chloroform layer is washed with water and dried over sodium sulfate.

Separation by silica-gel column-chromatography (eluted with chloroform) followed by recrystallization from ethanol gives the desired products example 31 (0.13 g) and example 32 (0.26 g).

What we claim is:

1. A compound selected from the group consisting of a free base and its acid addition salts, said free base having the formula wherein
each of $X_1$ and $X_2$ is chlorine;
$R_3$ is selected from the group consisting of hydrogen and phenyl;
and $R_2$ is selected from the group consisting of:
 (a) unsubstituted phenyl,
 (b) substituted phenyl having up to two substituents selected from the group consisting of an alkyl having 1–4 carbon atoms, methoxy, an alkoxy carbonyl having 1–3 carbon atoms, trifluoromethyl, and a halogen,
 (c) an alkyl having 1–2 carbon atoms which is substituted with a phenyl, said phenyl being selected from the group consisting of unsubstituted phenyl and substituted phenyl having up to two halogen substituents,
 (d) cinnamyl,
 (e) cyclohexyl,
 (f) cyclohexylmethyl, and
 (g) adamantyl.

* * * * *